United States Patent [19]

Polizzotto

[11] Patent Number: 4,561,846
[45] Date of Patent: Dec. 31, 1985

[54] DENTAL PANTOGRAPH
[75] Inventor: Joseph F. Polizzotto, Huntington Beach, Calif.
[73] Assignee: Denar Corporation, Anaheim, Calif.
[21] Appl. No.: 529,160
[22] Filed: Sep. 2, 1983
[51] Int. Cl.$^4$ .............................................. A61C 19/04
[52] U.S. Cl. ...................................... 433/73; 433/69; 250/237 G; 356/374; 33/125 C
[58] Field of Search ............................ 433/73, 69, 68; 250/237 G; 33/125 C; 356/374, 373

[56] References Cited
U.S. PATENT DOCUMENTS

| | | | |
|---|---|---|---|
| 3,675,331 | 7/1972 | Ernst et al. | 33/125 C |
| 4,014,097 | 3/1977 | Pameijer | 433/69 |
| 4,078,173 | 3/1978 | Fultz | 250/237 G |
| 4,158,509 | 6/1979 | Rieder et al. | 33/125 C |
| 4,330,276 | 5/1982 | Becker et al. | 433/69 |
| 4,354,836 | 10/1982 | Santoni | 433/73 |
| 4,385,836 | 5/1983 | Schmitt | 250/237 G |
| 4,386,405 | 5/1983 | Lewin et al. | 433/69 |
| 4,403,859 | 9/1983 | Ernst | 250/237 G |
| 4,447,207 | 5/1984 | Kataoka et al. | 433/69 |
| 4,495,952 | 1/1985 | Klett | 433/69 |

Primary Examiner—John J. Wilson
Attorney, Agent, or Firm—K. H. Boswell; Edward D. O'Brian

[57] ABSTRACT

A dental pantograph capable of measuring mandibulary movement includes right and left side housings have orthogonally located X, Y and Z scales. The housing further includes X, Y and Z scale transducers for reading reference marks on the respective scales. The scales are slidable with respect to the transducers. The housings are located adjacent to engagement members with one of the housing or the engagement member associated with the mandible and the other associated with the maxilla. The scales extend between the housing and the engagement member and move with respect to the transducers in the housing by movement between the housing and the engagement member. The transducers produce electrical output signals which are fed to an appropriate signal processor, such as a microprocessor, for producing a readout indicating the mandibulary movement.

29 Claims, 11 Drawing Figures

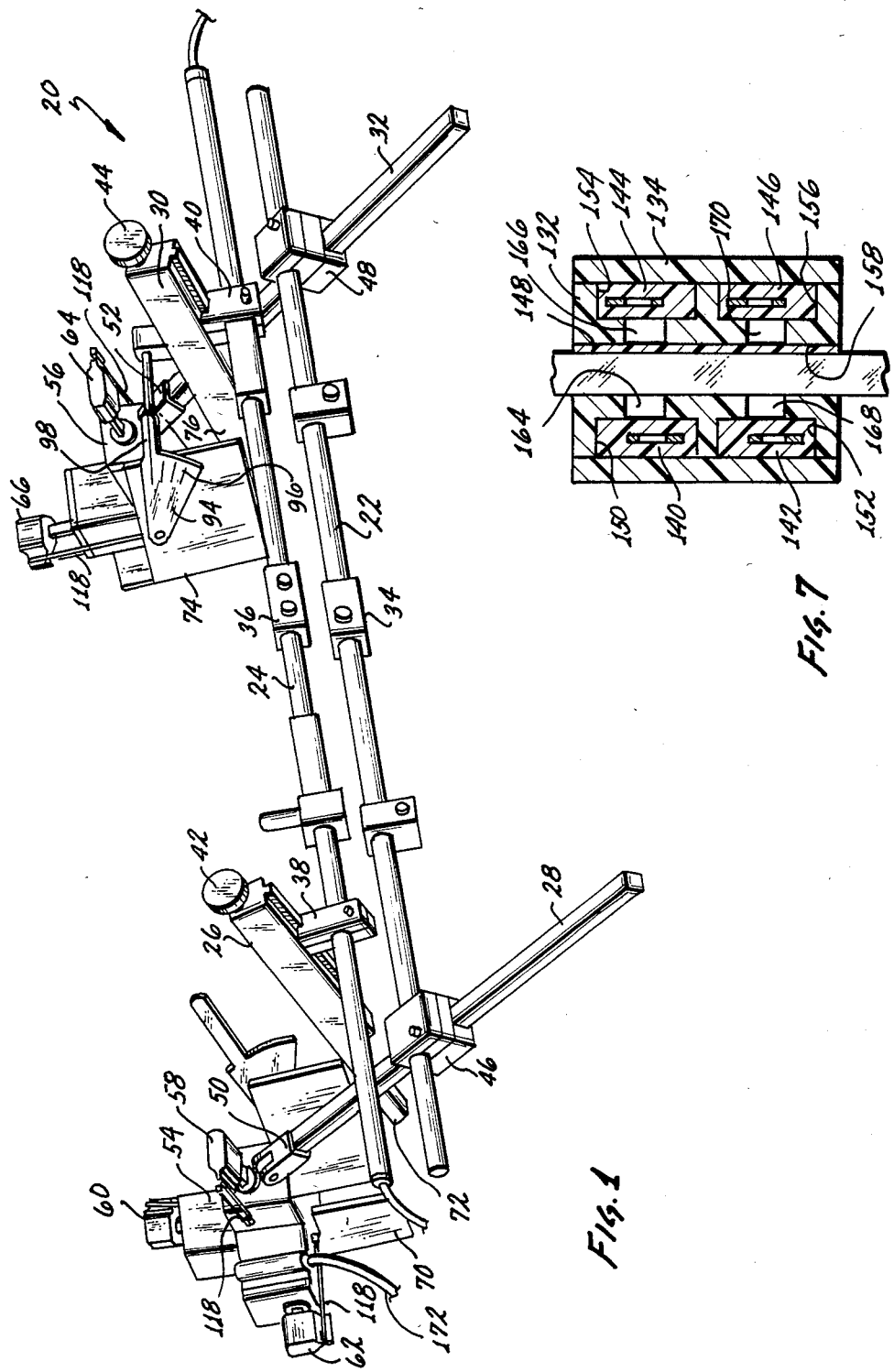

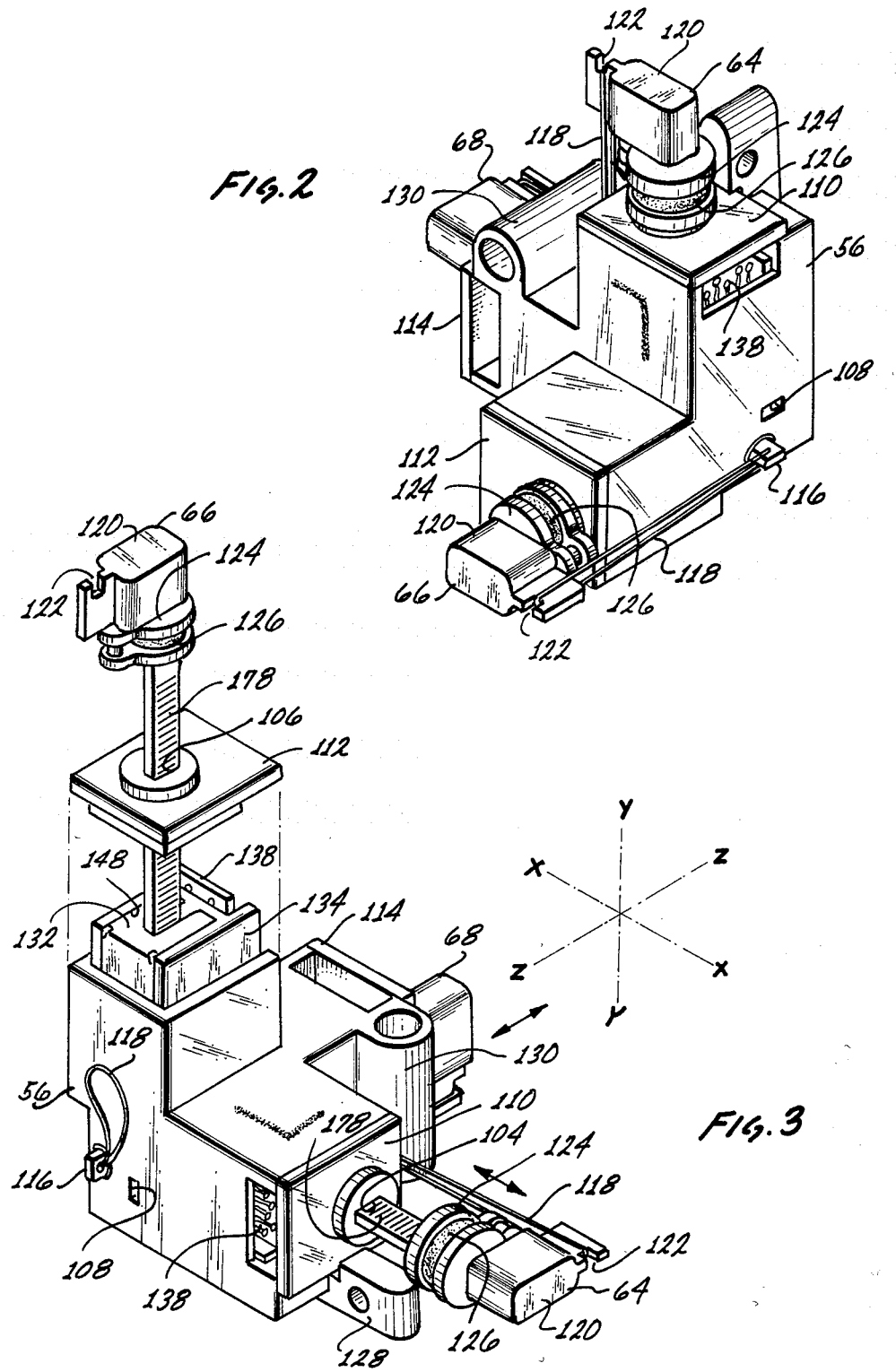

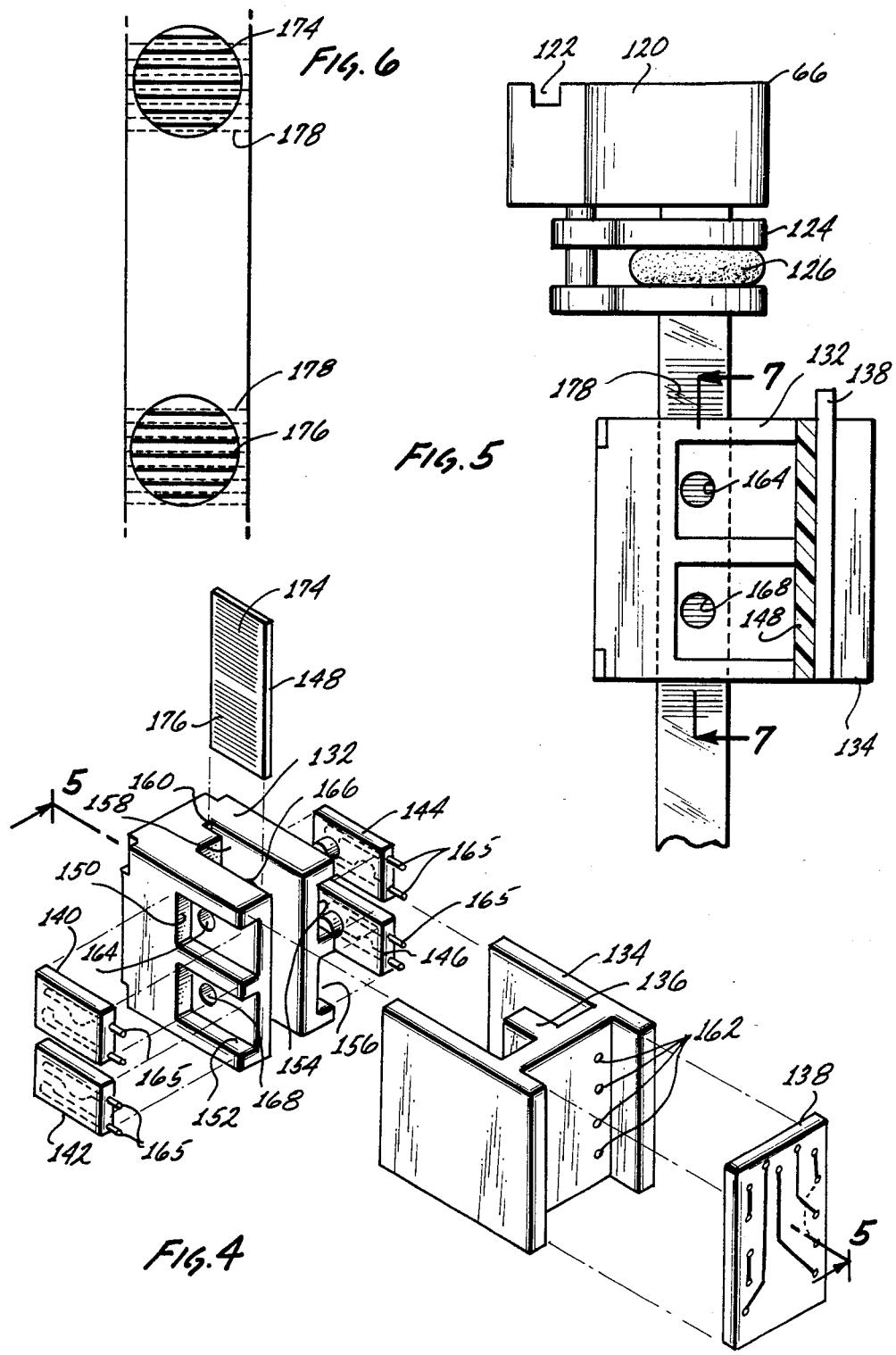

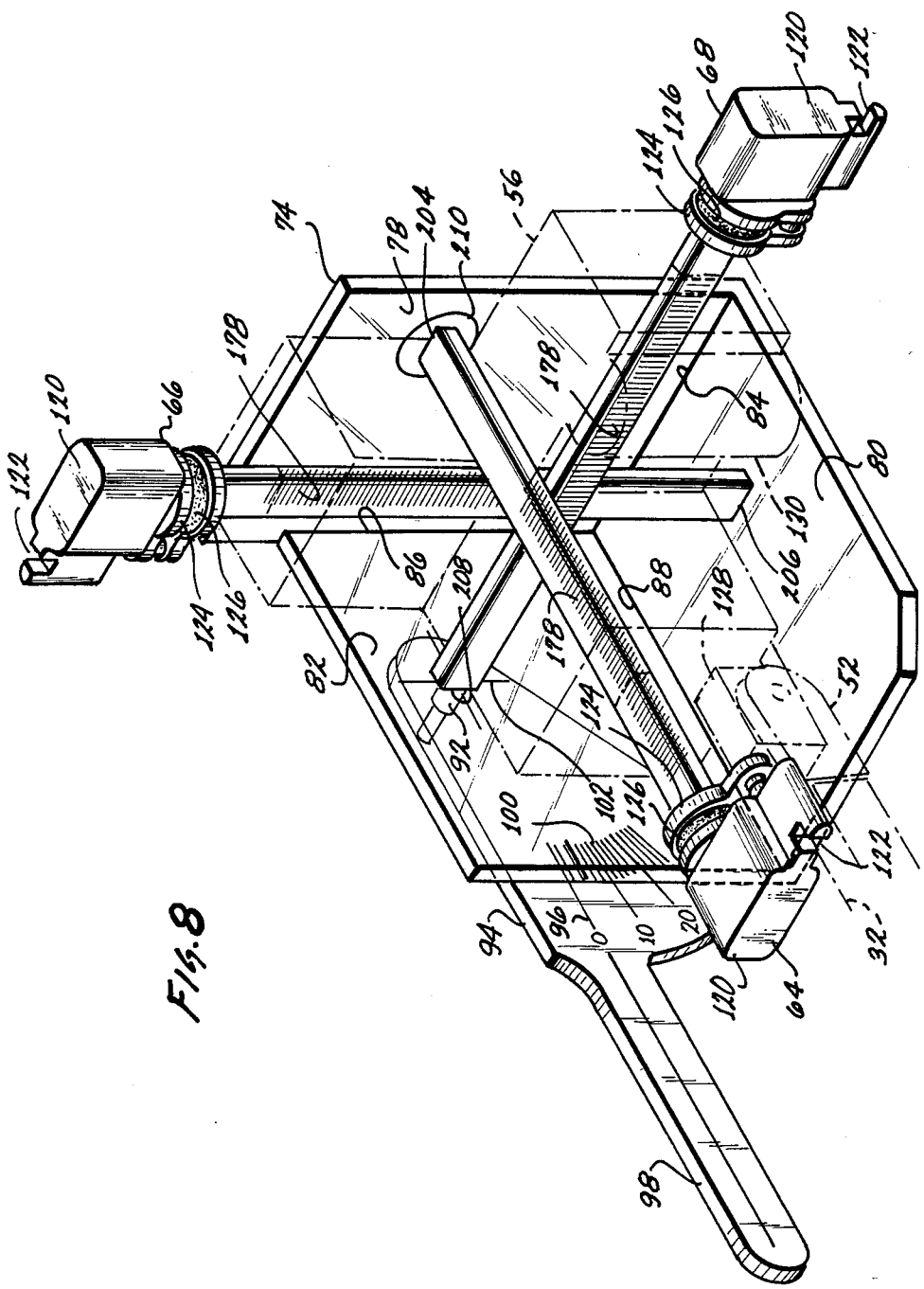

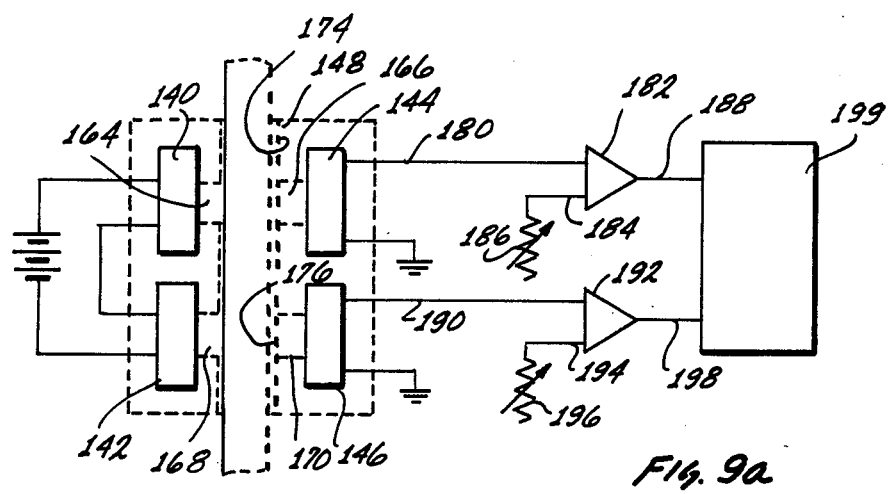
Fig. 9a
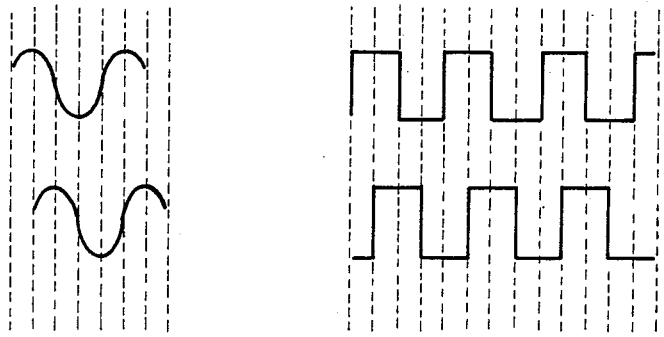
Fig. 9b
Fig. 9c
10011001 ⟵ 200
11001100 ⟵ 202

DENTAL PANTOGRAPH

BACKGROUND OF THE INVENTION

This invention relates to a dental Pantograph wherein movement of the mandible with respect to the maxilla is measured along three orthogonally positioned transducers located at each hinge axis of the temporomandibular joint. Measurements are made by the movement of the transducers made in response to movement of the mandible with respect to the maxilla.

The human jaw includes the lower jaw bone, the mandible, which is pivotally mounted to the upper jaw bone, the maxilla, at the temporomandibular joint. The attachment is via a loose ball and socket type joint wherein a fossa on both the right and left side of the maxilla receives a condyle on both the right and left side of the mandible.

The fit of the condyles in the fossa is rather loose, allowing for extensive movement of the mandible with respect to the maxilla. Not only can the mandible move up and down with respect to the maxilla, but it can be moved backward and forward in a protrusive pathway and laterally, side to side. In executing the lateral movement, these condyles on the side on which the mandible is moving executes a rotation, whereas the condyle on the side away from the direction of movement executes orbiting. Accompanying the orbiting and rotation of the condyles are mandibulary side shifts. As such, the locus of movement of the individual condyle are complex in nature.

The complex movement of the mandible has been studied over the years in order to better understand the manner in which the teeth fit or occlude with respect to one another. Certain temporomandibular joint dysfunctions are the direct result of misocclusion of the teeth. Such misocclusion can lead to pain and stress and train of the various muscles which support and move the mandible.

Over the years, certain device have been constructed in order to measure and mimic the movement of the mandible. Pantographs have been constructed to measure the mandible movement and articulators have been constructed in order to mimic the movement of the mandible outside of the mouth in order to study and construct dental appliances for treatment of malocclusion and the like.

Because of the complex movement of the mandible as outlined above, many different expedients have been resorted to in construction of pantographic devices which could best trace and record the parameters of movement of the mandible. Many of these devices could be described; however, it is sufficient to say for the purposes of this discussion that for the most part, these devices were exceedingly tedious to use and the reproducibility of the devices, while slowly improving over the years, still leave much to be desired.

The dentist who utilizes such pantographs is a highly skilled professional whose time is exceedingly valuable. The trial and error use of the prior known pantographic devices was exceedingly wasteful for dentists' time. Furthermore, in those prior pantographic devices which produced condylar path tracings, not only was it necessary to spend an exceedingly protracted length of time in obtaining the tracings, it was then further necessary to follow the condylar path tracings while adjusting the articulator until such time that the movement of the articulator precisely followed the condylar path tracings.

BRIEF DESCRIPTION OF THE INVENTION

In view of the above, it is evident that there exists a need for new and improved pantographs which eliminate the time consuming and tedious processes inherent in the existing pantographs. In view of this need, it is a broad object of this invention to provide a pantograph which provides a direct numerical readout to the operator of the same such that the readout can be directly entered to the dials of an articulator without having to attempt to follow condylar path tracings for setting the articulator. It is a further object of this invention to provide a pantograph whose use is rapid and accurate and thus further saves valuable professional time in obtaining the measurements of the condylar path movements. Additionally, it is an object of this invention to provide a pantograph which automatically records the condylar pathway during excursive movements of the mandible without necessitating extensive human readout of individual measuring devices.

These and other objects, as will become evident from the remainder of this specification are achieved in a pantograph device having a maxilla cross bow and a mandible cross bow with respective right and left side arms attaching to each of said maxilla and mandible cross bows with said respective mandible side arms moving with respect to said respective maxilla side arms in response to mandibulary movement an improvement which comprises: a right X axis scale; a right Y axis scale; a right Z axis scale; a left X axis scale; a left Y axis scale; a left Z axis scale; each of said scales being elongated and including a plurality of reference means located in a spaced array along their length; a right scale engagement means operatively connecting to one of said right side mandible and maxilla side arms, said right side scale engagement means for operatively associating said right X, Y and Z scales with said right side mandible and maxilla side arm to which said right side scale engagement means is operatively connected; a right scale orientation means operatively connecting to the other one of said right side mandible and maxilla side arms and positioned adjacent to but not in direct contact with said right scale engagement means, the one of said right scale engagement means and right scale orientation means operatively connected to the right side mandible side arm movable with respect to the one of said right scale engagement means and right scale orientation means operatively connected to said right side maxilla side arm in response to mandibulary movement, said right scale orientation means having orthogonal X, Y and Z axes, said right scale orientation means for orienting said right X, Y and Z scales with said right engagement means and for sensing said reference means on said right X, Y and Z scales; said right X axis scale operatively associated with said right scale orientation means and axially movable with respect to said right scale orientation means along said X axis and fixed against transverse movement with respect to said right scale orientation means along said Y and Z axes, said right X scale contacting said right engagement means and moving with respect to said right scale orientation means along said X axis in response to movement of said right side mandibulary side arm with respect to said right side maxillary side arm along said X axis; said right Y axis scale operatively associated with said right scale orientation means and axially movable with respect to said right scale orientation means along said Y axis and fixed against transverse movement with respect to said right scale orientation means along said X and Z axes, said right Y scale contacting said right engagement means and moving with respect to said right scale orientation means along said Y axis in response to movement of said right side mandibulary side arm with respect to said right side maxillary side arm along said Y axis; said right Z axis scale operatively associated with said right scale orientation means and axially movable with respect to said right scale orientation means along said Z axis and fixed against transverse movement with respect to said right scale orientation means along said X and Y axes, said right Z scale contacting said right engagement means and moving with respect to said right scale orientation means along said Z axis in response to movement of said right side mandibulary side arm with respect to said right side maxillary side arm along said Z axis; a left scale engagement means operatively connecting to one of said left side mandible and maxilla side arms, said left said scale engagement means for operatively associating said left X, Y and Z scales with said left side mandible and maxilla side arm to which said left side scale engagement means is operatively connected; a left scale orientation means operatively connecting to the other one of said left side mandible and maxilla side arms and positioned adjacent to but not in direct contact with said left scale engagement means, the one of said left scale engagement means and left scale orientation means operatively connected to the left side mandible side arm movable with respect to the one of said left scale engagement means and left scale orientation means operatively connected to said left side maxilla side arm in response to mandibulary movement, said left scale orientation means having orthogonal X, Y and Z axes, said left scale orientation means for orienting said left X, Y and Z scales with said left engagement means and for sensing said reference means on said left X Y and Z scales; said left X axis scale operatively associated with said left scale orientation means and axially movable with respect to said left scale orientation means along said X axis and fixed against transverse movement with respect to said left scale orientation means along said Y and Z axes, said left X scale contacting said left engagement means and moving with respect to said left scale orientation means along said X axis in response to movement of said left side mandibulary side arm with respect to said left side maxillary side arm along said X axis; said left Y axis scale operatively associated with said left scale orientation means and axially movable with respect to said left scale orientation means along said Y axis and fixed against transverse movement with respect to said left scale orientation means along said X and Z axes, said left Y scale contacting said left engagement means and moving with respect to said left scale orientation means along said Y axis in response to movement of said left side mandibulary side arm with respect to said left side maxillary side arm along said Y axis; said left Z axis scale operatively associated with said left scale orientation means and axially movable with respect to said left scale orientation means along said Z axis and fixed against transverse movement with respect to said left scale orientation means along said X and Y axes, said left Z scale contacting said left engagement means and moving with respect to said left scale orientation means along said Z axis in response to movement of said left side mandibulary side arm with respect to said left side maxillary side arm along said Z axis; right sensor means located on said right scale orientation means for sensing said reference means on said right X axis, Y axis and Z axis scales; left sensor means located on said left scale orientation means for sensing said reference means on said left X axis, Y axis and Z axis scales; each of said right sensor means and said left sensor means producing an output in response to sensing said reference means with said output indicating axial movement of said right X axis, Y axis and Z axis scales and said left X axis, Y axis and Z axis scales with respect to said right and left scale orientation means respectively in response to mandibulary movement.

Preferredly, a guide would be associated with each of the respective scales so as to guide those scales such that they can axially move with respect to the respective scale orientation means.

In the preferred embodiment, the right and left scale engagement means would each include three mutually perpendicular plates which are positioned in association with one another and with the respective guide means such that the plates are axially positioned from the guide means allowing the respective scales to move between the guide means and the plates. Further, in the preferred embodiment, the respective right and left scale orientation means would include a right and left housing with the respective guide means comprising openings located in the housing to allow the scales to move axially with respect to the housings. Further, biasing means would be associated with each of the scales with the housing means extending between the scales and their respective housings so as to bias the respective scales toward the respective plates.

In the preferred embodiment, the right and left sensor means in response to sensing the reference means would produce electrical signal corresponding to movements of their respective scales. Further, an electrical signal processing means would be operatively associated with the right and left sensor means so as to receive the electrical signals from the right and left sensor means and to produce an output corresponding to movement between the respective scale means and their associated sensor means. This movemeent is in response to mandibulary movement.

In the preferred embodiment, both the right and left sensor means would include a radiation transmitting means and a radiation receiving means each located in their respective housing and operatively associated with each other and with the reference mark on the respective scales. The radiation transmitting means would be capable of generating and propagating radiation toward the respective scales and the respective radiation receiving means would be capable of receiving this radiation and response to receipt of variations in the receipt of said radiation producing the electrical signals. The reference means, in interacting with the radiation transmitted by the radiation transmitting means would be capable, upon movement of the reference means, of causing a variation in the radiation further propagated toward the radiation receiving means.

Further in the preferred embodiment, the electrical signal processing means would include a digital logic device and a digitizing means capable of digitizing the electrical signals such that they can be processed by the digital logic device.

In the preferred embodiment, for measuring both direction of movement as well as degree of movement of each of the respective scales, each of the respective scales would include a first and a second radiation receiver associated with it. The first radiation receiver would receive radiation which has interacted with a first portion of the reference marks on any particular scale with the second radiation receiver responding to radiation which has interacted with a second portion of those reference marks. Each of the first and second radiation receivers would be capable of producing an electrical output in response to receipt of radiation. Further, the electrical outputs received from the first and the second radiation receivers associated with any particular scale would be out of phase with one another, preferredly 90 degrees out of phase.

Preferredly, the radiation is electromagnetic radiation, more preferredly in the wave length range of light radiation. As such, the radiation transmittors would preferredly comprise light emitting diodes and the radiation receivers would preferredly comprise photosensitive transistors.

Preferredly, each of the scales would be formed of a transparent material with the reference marks constituting opaque marks located along the scales. In addition, a reference scale can be associated with each of the scales with a second set of reference marks located on the reference scale. Preferredly, this second set of reference marks is divided into a first and second section, with the reference marks in the first section being displaced with respect to the reference marks in the second section.

BRIEF DESCRIPTION OF THE DRAWINGS

This invention will be better understood when taken in conjunction with the drawings wherein:

FIG. 1 is an isometric view of a pantograph incorporating the principles of this invention;

FIG. 2 is an isometric view of a portion of the invention shown in FIG. 1;

FIG. 3 is an isometric view similar to FIG. 2 except taken at a different angle and with certain of the components attaching thereto exploded from the remainder of the components;

FIG. 4 is a further explosion of a portion of the components seen in FIG. 3;

FIG 5 is a side elevational view in partial section about the line 5—5 of FIG. 4;

FIG. 6 is an enlarged view of a portion of FIG. 5;

FIG. 7 is a side elevational view in partial section about the line 7—7 of FIG. 5;

FIG. 8 is an isometric view of a portion of the invention seen in FIG. 1 with certain overlaying components removed to show interaction of other components;

FIG. 9a is a representational view, including certain schematic circuit elements of operation of the invention;

FIG. 9b is a symbolic depiction of certain wave forms of certain of the elements seen in FIG. 9a with phantom lines utilized to align the wave forms; and FIG. 9c is a symbolic depiction of certain logic states aligned with the phantom lines of FIG. 9b to correlate these states with the wave forms of FIG. 9b.

This invention utilizes certain principles and/or concepts as are set forth in the claims appended to this specification. These principles and/or concepts are capable of being utilized in a variety of embodiments differing from the exact illustrative embodiment utilized for illustrative purposes herein. For this reason, this invention is not to be construed as being limited to the exact illustrative embodiment but is only to be construed as being limited by the claims.

DETAILED DESCRIPTION OF THE INVENTION

In FIG. 1 a dental pantograph 20 is shown. Collectively making up the dental pantograph would be a mandible cross bow 22, a maxilla cross bow 24, a right side (as viewed from the patient's head) maxilla side arm 26, a right side mandible side arm 28, a left side maxilla side arm 30 and a left side mandible side arm 32. The cross bows and side arms 22, 24, 26, 28, 30 and 32 are essentially standard in appearance and function as per existing dental articulators.

Approximate maxilla and mandible clutches, not shown or numbered, would attach to the cross bows 24 and 22 at attachment junctions 34 and 36, respectively, on the respective cross bows. Insofar as such clutches are known in the art, for brevity of this specification, they are neither shown nor described.

The maxilla side arms 26 and 30 are attached to the maxilla cross bow 24 at junction members 38 and 40, respectively, and are adjustable with respect to the cross bow 24 via knurled knobs 42 and 44, allowing for correct hinge axis alignment, as hereinafter explained, of the maxilla side arms 26 and 30. The maxilla side arms 26 and 30 are movable backward and forward via the knurled knobs 42 and 44 and can be rotated about the cross bow 24 via the junction members 38 and 40 to align components as hereinafter described along the hinge axis of the right and left temporomandibular joints of the patient.

Likewise, the mandible side arms 28 and 32 are attached to the mandible cross bow 22 via junction members 46 and 48 with backward and forward and rotational movement of these arms 28 and 32 with respect to the cross bow 22 accomplished via loosening and tightening of the junction members 46 and 48.

With the pantograph 20 correctly placed with respect to the patient's jaw and with certain components which attach to the maxilla and mandible side arms 26, 28, 30 and 32 correctly positioned as hereinafter explained, the practitioner guides the patient's jaw through standard excrusive movements to move the patients's mandible with respect to his maxilla such that the mandible movements are transferred via the above described clutches to the mandible cross bow 22. Movement of the maxilla cross bow 22 with respect to the mandible cross bow 24 results in corresponding movement of the mandible side arms 28 and 32 with respect to the maxilla side arms 26 and 30. In response to mandibulary movement the temporomandibular joint ends 50 and 52 of the respective mandible side arms 28 and 32 move in pathways which can be broken down in a three dimensional coordinate system along X, Y and Z axes.

By measuring the movement of the ends 50 and 52 (or more accurately, movement of other components as hereinafter explained attached to these ends) along the X,Y and Z axes with respect to the stationary maxilla side arms 26 and 30 (or more accurately, other components as hereinafter explained attached to these side arms 26 and 30) movement of the right and left mandibulary condyles in the respective right and left temporomandibular joints can be ascertained.

A right scale housing 54 attaches to the end 50 of the right mandible side arm 28. Likewise, a left scale housing 56 attaches to the end 52 of the left mandible side arm 32. The housings 54 and 56 are mirror images of one another. In view of this, detailed description of only one of the housings, housing 56, will suffice for describing both of the housings, with the only difference being the spatial orientation with respect to the mirror imagery between the two housings 54 and 56.

A right side X axis scale 58, Y axis scale 60 and Z axis scale 62 are slidably mounted to the housing 54. Likewise, a left X axis scale 64, Y axis scale 66 and Z axis scale 68 are movably mounted to the left scale housings 56. The right scales 58, 60 and 62 function as per the left scales 64, 66 and 68 except for the same mirror imagery which exists between the housings 54 and 56. For the same reason then, only the scales 64, 66 and 68 will be described in detail, with the function of the other scales 58, 60 and 62 working in an equivalent manner except on the right side of the apparatus 20.

A right side engagement member 70 attaches to end 72 of the right side maxilla side arm 26. Likewise, a left side engagement member 74 attaches to end 76 of the left side maxilla side arm 30. As with the housings 54 and 56, a mirror imagery exists between the engagement members 70 and 74. For this reason, only the engagement member 74 will be described in detail. The equivalent parts, except for the mirror imagery exist on the engagement member 70 but in the interest of brevity will not be described.

Referring now to FIG. 8, the member 74 is seen in detail. The member 74 is composed of a X axis plate 78, a Y axis plate 80 and a Z axis plate 82 which are integrally formed together, preferredly from a transparent resin such that the plates 78, 80 and 82 are orthogonally located with respect to one another with side edge 84 being a mutual edge between plates 80 and 78 along the X axis, side edge 86 being a mutual edge between the plates 78 and 82 along the Y axis and side edge 88 being a mutual edge between the plates 80 amd 82 along the Z axis. Together, the plates 78, 80 and 82 form three sides of a box-like structure with the angles between the edges 86, 88 and 90 being respective right angles.

A small boss 92 is located on plate 82 and projects outwardly along an X axis in a direction toward the head of the patient. A transparent protractor 94 having suitable indicia 96 located thereon is hinged about the boss 92 to the engagement member 74. The protractor 94 includes a horizontal aligning arm 98 and the plate 82 includes a reference mark 100 which is utilized in conjunction with the indicia 96. Centering indicia 102 are printed on the plate 88 about the center of the boss 92.

The right and left hinge axis of the mandible are appropriately located on the patients head utilizing normal techniques. Further, a horizontal alignment line is also located. The engagement members 70 and 74 are then positioned with respect to the right and left hinge axis as follows for the engagement member 74. The boss 92 is centered at the hinge axis mark and the horizontal alignment arm 98 is aligned with the horizontal mark. The starting angle of the maxilla side arm 30 can then be read off the protractor 94 with respect to the reference line 100.

Referring now to FIGS. 2 through 7, the housing 56 and the scales 64, 66 and 68 and other components attached thereto are shown. In FIG. 3 the housing 58 is oriented essentially as seen in FIG. 2. In moving from FIG. 3 to FIG. 2 the housing 58 has been rotated 90 degrees twice about axis which are perpendicular. For FIG. 4, certain other components which are seen in the exploded part of FIG. 3 have been withdrawn from the interior of the housing 56 and exploded with respect to one another so as to further illustrate the construction of the same. For FIG. 5 the scale 66 has then been added to these components to show the relationship of the scales to the components. A portion of FIG. 5 is then enlarged within FIG. 6 and a sectional view taken at a different angle about the line 7—7 of FIG. 5 seen in FIG. 7.

Displaced to the right hand side of FIG. 3 in phantom line is a set of coordinates showing positioning of the housing 56 with respect to an X, Y and Z axis. Along the X axis, the scale 64 fits into an X axis passageway 104 which extends through the housing 56 along the X axis. Similarly, the scale 66 fits into a Y axis passageway 106 with the scale 68 fitting into a Z axis passageway 108. In FIG. 3 one end of the passageways 104 and 106 for the scales 64 and 66 are seen, whereas the opposite end of the passageway 108 for scale 68 is seen.

The housing 56 has three hollow chambers corresponding to the X, Y and Z axes in which a set of components, one of which is illustrated in FIG. 4, are inserted. Caps 110, 112 and 114 fit over these hollow chambers with a portion of the passageways 104, 106 and 108 formed in each of the respective caps 110, 112 and 114. Three identical small ears, only one of which can be seen, ear 116, are strategically located on the housing 56. The ears 106 have a small opening, not separately identified or numbered, located therein allowing for attachment of a small rubber band, collectively identified by the numeral 118, thereto.

Each of the scales 58, 60, 62, 64, 66 and 68, have a head, collectively identified by the numeral 120 which includes a small slot 122 located thereon. The rubber bands 118 fit into the slots 122 and thus bias the respective scales toward the ears 116. Thus, in FIG. 2, for the rubber band 118 which is seen attached to the ear 116, the scale 66 is biased such that its head 120 is urged to move toward the projection 116.

Each of the respective scales further includes a positioning member 124 having an O ring 126 located therein. The respective scales slide through the positioning member 124 with the O ring 126 chosen such that it is capable of gripping along the shaft of the respective scales of fixedly hold the positioning member 124 at any position on the respective scales. The positioning member 124 can be slid along the length of the scale to which it is attached by the practitioner during initial alignment of the housing 54 or 56 with its respective engagement members 70 or 74 as hereinafter explained.

The housing 56 has an attachment projection 108 integrally molded thereon which attaches to the end 52 of the mandible side arm 32. The housing 56 further includes an elongated ear 130 which serves as a cable attachment point for connecting electrical lead lines to the housing 56.

A set of components as illustrated in FIG. 4 fit underneath each of the caps 110, 112 and 114 as previously noted. The Y axis set of the components is partly exploded out of the housing 56 in FIG. 3 and fully extended in FIG. 4. These components include a U shaped member 132, a distorted H shaped member 134 having a web 136 in its center, a small printed circuit board 138, two light emitting diodes 140 and 142, two light sensitive transistors 144 and 146 and a fixed scale or reference scale 148.

The member 132 has four recessed areas 150, 152, 154 and 156, which are sized and shaped so as to accept the components 140, 142, 144 and 146, respectively. The member 132 further includes a central channel 158. The web 136 fits into a portion of the channel 158 with the 68 are slid in the housing 56 against the bias of the rubber bands 118 to disengage the ends 204, 206 and 208 from the plates 78, 80 and 82, respectively. The scales 64, 66 and 68 are then fixed in this position by sliding the positioning member 124 along the scales. The practitioner can now align the housing 58 with respect to the engagement member 74 by movement about clamp 46 to position the axial axis of the scale 68 with respect to the reference marks 102 and the axial axis of the scale 64 with respect to a reference circle 210 printed on the plate 78. The positioning members 124 are systematically withdrawn back toward the heads of the scales 120 as this alignment is done, stepwise allowing the respective scales 68, 64 and then 66 to engage the plates 82, 78 and 80. The pantographic device 20 is now ready for measurement of the mandibulary movement.

If, in executing the different movements which are being measured, the practitioner moves the patient's jaw too far, and then moves the jaw back in the opposite direction to an intermediate position, the particular scales which are involved in this movement move first in one direction with respect to their photo sensors and then back in the other direction. Insofar as the voltage comparators 182 and 192 sense direction of movement of the scales, the movement past a particular point and then back again to that point is automatically compensated for by the above noted direction detection indicated by the comparison of the change of state between the outputs of the voltage comparators 182 and 192.

If, for instance, the practitioner moved the patient's jaw such that the housing 56 moved five millimeters with respect to the scale 64, but in fact this was two millimeters too much, and then the practitioner moved the patient's jaw such that the housing 56 moved back two millimeters along the scale 64, the direction reading ability of the device 20 would sense this two directional movement and correctly read out the final position of three millimeters. This is in comparison to other devices not having this directional reading ability which would first record the five millimeter movement and then upon the subsequent two millimeter movement, add this to the five to give an erroneous readout of seven millimeters.

For the purposes of illustration herein, the engagement members 70 and 74 have been attached to the maxilla side arms 26 and 30 with the housings 54 and 56 attaching to the mandible side arms 28 amd 32. It is apparent that, instead of this physical setup, the engagement members 70 and 74 could be attached to the mandible side arms 28 and 32 and movable with respect to mandibulary movement with the housings 54 and 56 attached to the maxilla side arms 26 and 30 and fixed with respect to mandibulary movement. In this instances, the housings 54 and 56 would be stationary with respect to mandibulary movement, but the individual scales 58, 60, 62, 64, 66 and 68 would move in direct response to appropriate mandibulary movement. It is considered preferred, however, to attach the engagement members 70 and 74 to the fixed maxilla side arms 28 and 30 to facilitate alignment of the housings 54 and 56 and the engagement members 70 and 74 with respect to the temporomandibular joints.

I claim:

1. In a pantograph device having a maxilla cross bow and a mandible cross bow with respective right and left side arms attaching to each of said maxilla and mandible cross bows with said respective mandible side arms moving with respect to said respective maxilla side arms in response to mandibulary movement an improvement which comprises:

a right X axis scale;
a right Y Axis scale;
a right Z axis scale;
a left X axis scale;
a left Y axis scale;
a left Z axis scale;
each of said scales being elongated and including a plurality of reference means located in a spaced arrray along their length;
a right scale engagement means operatively connecting to one of said right side mandible and maxilla side arms, said right side scale engagement means for operatively associating said right X, Y and Z scales with said right side mandible and maxilla side arm to which said right side scale engagement means is operatively connected;
a right scale orientation means operatively connecting to the other one of said right side mandible and maxilla side arms and positioned adjacent to but not in direct contact with said right scale engagement means, the one of said right scale engagement means and right scale orientation means operatively connected to the right side mandible side arm movable with respect to the one of said right scale engagement means and right scale orientation means operatively connected to said right side maxilla side arm in response to mandibulary movement, said right scale orientation means having orthogonal X, Y and Z axes, said right scale orientation means for orienting said right X, Y and Z scales with said right engagement means and for sensing said reference means on said right X, Y and Z scales;
said right X axis scale operatively associated with said right scale orientation means and axially movable with respect to said right scale orientation means along said X axis and fixed against transverse movement with respect to said right scale orientation means along said Y and Z axes, said right X scale contacting said right engagement means and moving with respect to said right scale orientation means along said X axis in response to movement of said right side mandibulary side arm with respect to said right side maxilary side arm along said X axis;
said right Y axis scale operatively associated with said right scale orientation means and axially movable with respect to said right scale orientation means along said Y axis and fixed against transverse movement with respect to said right scale orientation means along said X and Z axes, said right Y scale contacting said right engagement means and moving with respect to said right scale orientation means along said Y axis in response to movement of said right side mandibulary side arm with respect to said right side maxillary side arm along said Y axis;
said right Z axis scale operatively associated with said right scale orientation means and axially movable with respect to said right scale orientation means along said Z axis and fixed against transverse movement with respect to said right scale orientation means along said X and Y axes, said right Z scale contacting said right engagement means and moving with respect to said right scale orientation means along said Z axis in response to movement of said right side mandibulary side arm with respect to said right side maxillary side arm along said Z axis;

a left scale engagement means operatively connecting to one of said left side mandible and maxilla side arms, said left scale engagement means for operatively associating said left X, Y and Z scales with said left side mandible and maxilla side arm to which said left side scale engagement means is operatively connected;

a left scale orientation means operatively connecting to the other one of said left side mandible and maxilla side arms and positioned adjacent to but not in direct contact with said left scale engagement means, the one of said left scale engagement means and left scale orientation means operatively connected to the left side mandible side arm movable with respect to the one of said left scale engagement means and left scale orientation means operatively connected to said left side maxilla side arm in response to mandibulary movement, said left scale orientation means having orthogonal X, Y and Z axes, said left scale orientation means for orienting said left X, Y and Z scales with said left engagement means and for sensing said reference means on said left X Y and Z scales;

said left X axis scale operatively associated with said left scale orientation means and axially movable with respect to said left scale orientation means along said X axis and fixed against transverse movement with respect to said left scale orientation means along said Y and Z axes, said left X scale contacting said left engagement means and moving with respect to said left scale orientation means along said X axis in response to movement of said left side mandibulary side arm with respect to said left side maxilary side arm along said X axis;

said left Y axis scale operatively associated with said left scale orientation means and axially movable with respect to said left scale orientation means along said Y axis and fixed against transverse movement with respect to said left scale orientation means along said X and Z axes, said left Y scale contacting said left engagement means and moving with respect to said left scale orientation means along said Y axis in response to movement of said left side mandibulary side arm with respect to said left side maxillary side arm along said Y axis;

said left Z axis scale operatively associated with said left scale orientation means and axially movable with respect to said left scale orientation means along said Z axis and fixed against tranverse movement with respect to said left scale orientation means along said X and Y axes, said left Z scale contacting said left engagement means and moving with respect to said left scale orientation means along said Z axis in response to movement of said left side mandibulary side arm with respect to said left side maxillary side arm along said Z axis;

right sensor means located on said right scale orientation means for sensing said reference means on said right X axis, Y axis and Z axis scales;

left sensor means located on said left scale orientation means for sensing said reference means on said left X axis, Y axis and Z axis scales;

each of said right sensor means and said left sensor means producing an output in response to sensing said reference means with said output indicating axial movement between said right X axis, Y axis and Z axis scales and said left X axis, Y axis and Z axis scales and said right and left scale orientation means respectively in response to mandibulary movement.

2. The device of claim 1 wherein:

said right scale orientation means includes a right X scale guide means, right Y scale guide means and right Z scale guide means and said left scale orientation means includes a left X scale guide means, left Y scale guide means and left Z scale guide means, said right X, Y and Z scales and said left X, Y and Z scales movably associated with each of their respective scale guide means to move axially with respect to said guide means.

3. The device of claim 2 wherein:

said right scale engagement means includes right X, Y and Z plate means mutually orthogonally positioned with respect to one another, said right X plate means positioned axially along said X axis from said right X scale guide means with said right X scale extending between said right X scale guide means and said right X plate means, said right Y plate means positioned axially along said Y axis from said right Y scale guide means with said Y scale extending between said right Y scale guide means and said right Y plate means, said right Z plate means positioned axially along said Z axis from said right Z scale guide means with said right Z scale extending between said right Z scale guide means and said right Z plate means;

said left scale engagement means includes left X, Y and Z plate means mutually orthogonally positioned with respect to one another, said left X plate means positioned axially along said X axis from said left X scale guide means with said left X scale extending between said left X scale guide means and said left X plate means, said left Y plate means positioned axially along said Y axis from said left Y scale guide means with said left Y scale extending between said left Y scale guide means and said left Y plate means, said left Z plate means positioned along said Z axis from said left Z scale guide means with said left Z scale extending between said left Z scale guide means and said left Z plate means.

4. The device of claim 3 wherein:

said right scale orientation means includes a right housing and said left scale orientation means includes a left housing;

said right X, Y and Z scale guide means comprising said right housing having orthogonally positioned X, Y and Z openings passing through said housing axially along the respective X, Y and Z axes;

said left X, Y and Z scale guide means comprising said left housing having orthogonally positioned X, Y and Z openings passing through said housing axially along the respective X, Y and Z axes;

said right X, Y and Z scales positioned axially within said respective X, Y and Z openings in said right housing and movable in said respective openings toward and away from said respective X, Y and Z right plate means;

said left X, Y and Z scales positioned axially within said respective X, Y and Z openings in said left housing and movable in said respective openings toward and away from said respective X, Y and Z left plate means.

5. The device of claim 4 wherein:

said right scale orientation means includes X scale biasing means, Y scale biasing means and Z scale biasing means attaching between said right housing and said right X, Y and Z scales respectively and biasing said right X, Y and Z scales respectively towards said right X, Y and Z plate means respectively;

said left scale orientation means includes X scale biasing means, Y scale biasing means and Z scale biasing means attaching between said left housing and said left X, Y and Z scales respectively and biasing said left X, Y and Z scales respectively towards said left X, Y and Z plate means respectively.

6. The device of claim 5 wherein:

each of said right X, Y and Z plate means comprise a planar plate having at least two edges which are located at a right angle with respect to one another with said X, Y and Z plates joined together about their two said respective edges so as together one of said edges of each of said plates is common to one of said edges of each of the other of said plates;

each of said left X, Y and Z plate means comprise a planar plate having at least two edges which are located at a right angle with respect to one another with said X, Y and Z plates joined together about their two said respective edges so as together one of said edges of each of said plates is common to one of said edges of each of the other of said plates.

7. The device of claim 6 wherein:

said right and left sensor means in response to sensing said reference means produce electrical signals corresponding to the movement between said right and left X, Y and Z axes scales and said right and left sensor means respectively;

electrical signal processing means operatively associated with said right and left sensor means so as to receive said electrical signal from said right and left sensor means, said electrical signal processing means for producing a readout of the position of said right and left X, Y and Z axes scales with respect to movement between said respective scales and said right and left sensor means in resonse to mandibulary movement.

8. The device of claim 7 wherein:

said right sensor means includes a right radiation transmitting means and a right radiation receiving means each located on said right side housing and each operatively associated with each other and with said reference means on said right X, Y and Z axes scales, said right radiation transmitting means for generating and propagating radiation, said right radiation receiving means for receiving said radiation and producing an electrical signal in response to variations in receipt of said radiation;

said left sensor means including a left radiation transmitting means and a left radiation receiving means each located on said left side housing and each operatively associated with each other and with said reference means on said left X, Y and Z axes scales, said left radiation transmitting means for generating and propagating radiation, said left radiation receiving means for receiving said radiation and producing an electrical signal in response to variations in receipt of said radiation;

said reference means on each of said right X, Y and Z axes scales interacting with said radiation transmitted by said right radiation transmitting means upon movement of said scales with respect to said right housing to cause said variation in said radiaton received by said right radiation receiving means;

said reference means on each of said left X, Y and Z axes scales interacting with said radiation transmited by said left radiation transmitting means upon movement of said respective scales and said left housing to cause said variation in radiation received by said left radiation receiving means.

9. The device of claim 8 wherein:

said electrical signal processing means includes digitizing means operatively connected to said right and said left radiation receiving means so as to receive said electrical signals from said respective receiving means, said digitizing means for digitizing said electrical signals;

said electrical signal processing means includes a digital logic device.

10. The device of claim 9 wherein:

said right radiation receiving means includes a first and a second X axis radiation receiver each operatively associated with said right X axis scale, a first and a second Y axis radiation receiver each operatively associated with said Y axis scale, a first and a second Z axis radiation receiver each operatively associated with said right Z axis scale, each of said first and said second radiation receivers capable of producing an electrical signal upon receipt of said radiation, each of said first radiation receivers receiving radiation which has interacted with a first portion of said reference means on said respective right X, Y and Z axes scales with which it is associated and each of said second radiation receivers receiving radiation which has interacted with a second portion of said reference means on said respective scale with which it is associated;

said left radiation receiving means includes a first and a second X axis radiation receiver each operatively associated with said left X axis scale, a first and a second Y axis radiation receiver each operatively associated with said left Y axis scale, a first and a second Z axis radiation receiver each operatively associated with said left Z axis scale, each of said first and said second radiation receivers capable of producing an electrical signal upon receipt of said radiation, each of said first radiation receivers receiving radiation which has interacted with a first portion of said reference means on said respective left X, Y and Z axes scales with which it is associated and each of said second radiation receivers receiving radiation which has interacted with a second portion of said reference means on said respective scale with which it is associated;

each of said first radiation receivers producing a first electrical output signal in response to receipt of said radiation, each of said second radiation receivers producing a second electrical output signal in response to receipt of said radiation;

said electrical output signal from said first radiation receiver associated with each of said respective scales is out of phase with respect to the electrical output signal from said second radiation receiver associated with said respective scale.

11. The device of claim 10 wherein:

said phase difference between said electrical signals produced by said respective first and second radiation receiver associated with each respective scale is 90 degrees;

said radiation is light radiation.

12. The device of claim 11 wherein:
said right radiation transmitting means includes first and second X axis, Y axis and Z axis scale light emitting diodes;
said left radiation transmitting means includes first and second X axis, Y axis and Z axis scale light emitting diodes;
said first and said second radiation receivers associated with each of said respective scales comprise first and second photosensitive transistors.

13. The device of claim 12 wherein:
each of said respective scales include at least a portion thereof being formed of a light transparent material;
said reference means comprising light opaque markers on said transparent material;
a right X, Y and Z axis scale reference scale means located in said right housing and respectively associated with said right scales and located between said respective scales and their respective first and second photosensitive transistors;
left X, Y and Z axis scale reference scale means located in said left housing and respectively associated with said left scales and located between said respective scales and their respective first and second photosensitive transistors.

14. The device of claim 1 wherein:
said right and left sensor means in response to sensing said reference means produce electrical signals corresponding to the movement between said right and left X, Y and Z axes scales and said right and left sensor means respectively;
electrical signal processing means operatively associated with said right and left sensor means so as to receive said electrical signal from said right and left sensor means, said electrical signal processing means for producing a readout of the position of said right and left X, Y and Z axes scales with respect to movement between said respective scales and said right and left sensor means in resonse to mandibulary movement.

15. The device of claim 14 wherein:
said right scale orientation means includes a right side housing;
said left scale orientation means includes a left side housing.

16. The device of claim 15 wherein:
said right sensor means includes a right radiation transmitting means and a right radiation receiving means each located on said right side housing and each operatively associated with each other and with said reference means on said right X, Y and Z axes scales, said right radiation transmitting means for generating and propagating radiation, said right radiation receiving means for receiving said radiation and producing an electrical signal in response to variations in receipt of said radiation;
said left sensor means including a left radiation transmitting means and a left radiation receiving means each located on said left side housing and each operatively associated with each other and with said reference means on said left X, Y and Z axes scales, said left radiation transmitting means for generating and propagating radiation, said left radiation receiving means for receiving said radiation and producing an electrical signal in response to variations in receipt of said radiation;
said reference means on each of said right X, Y and Z axes scales interacting with said radiation transmitted by said right radiation transmitting means upon movement of said scales with respect to said right housing to cause said variation in said radiation received by said right radiation receiving means;
said reference means on each of said left, X, Y and Z axes scales interacting with said radiation transmitted by said left radiation transmitting means upon movement of said respective scales with respect to said left housing to cause said variation in radiation received by said left radiation receiving means.

17. The device of claim 16 wherein:
said electrical signal processing means includes digitizing means operatively connected to said right and said left radiation receiving means so as to receive said electrical signals from said respective receiving means, said digitizing means for digitizing said electrical signals.

18. The device of claim 17 wherein :
said electrical signal processing means includes a digital logic device.

19. The device of claim 18 wherein:
said right X, Y and Z scale guide means are located on said right side housing;
said left X, Y and Z scale guide means are located on said left side housing.

20. The device of claim 19 wherein:
said right radiation receiving means includes a first and a second X axis radiation receiver each operatively associated with said right X axis scale, a first and a second Y axis radiation receiver each operatively associated with said Y axis scale, a first and a second Z axis radiation receiver each operatively associated with said right Z axis scale, each of said first and said second radiation receivers capable of producing an electrical signal upon receipt of said radiation, each of said first radiation receivers receiving radiation which has interacted with a first portion of said reference means on said respective right X, Y and Z axes scales with which it is associated and each of said second radiation receivers receiving radiation which has interacted with a second portion of said reference means on said respective scale with which it is associated;
said left radiation receiving means includes a first and a second X axis radiation receiver each operatively associated with said left X axis scale, a first and a second Y axis radiation receiver each operatively associated with said left Y axis scale, a first and a second Z axis radiation receiver each operatively associated with said left Z axis scale, each of said first and said second radiation receivers capable of producing an electrical signal upon receipt of said radiation, each of said first radiation receivers receiving radiation which has interacted with a first portion of said reference means on said respective left X, Y and Z axes scales with which it is associated and each of said sceond radiation receivers receiving radiation which has interacted with a second portion of said reference means on said respective scale with which it is associated;
each of said first radiation receivers producing a first electrical output signal in response to receipt of said radiation, each of said second radiation receivers producing a second electrical output signal in response to receipt of said radiation.

21. The device of claim 20 wherein:

said electrical output signal from said first radiation receiver associated with each of said respective scales is out of phase with respect to the electrical output signal from said second radiation receiver associated with said respective scale.

22. The device of claim 21 wherein:
said phase difference between said electrical signals produced by said respective first and second radiation receiver associated with each respective scale is 90 degrees.

23. The device of claim 22 wherein:
said radiation is electromagnetic radiation.

24. The device of claim 23 wherein:
said radiation is light radiation.

25. The device of claim 24 wherein:
said right radiation transmitting means includes first and second X axis, Y axis and Z axis scale light emitting diodes;
said left radiation transmitting means includes first and second X axis, Y axis and Z axis scale light emitting diodes.

26. The device of claim 25 wherein:
said first and said second radiation receivers associated with each of said respective scales comprise first and second photosensitive transistors.

27. The device of claim 26 wherein:
each of said respective scales include at least a porion thereof being formed of a light transparent material;
said reference means comprising light opaque markers on said transparent material.

28. The device of claim 27 including:
a right X, Y and Z axis reference scale means located in said right housing and respectively associated with said right scales and located between said respective scales and their respective first and second photosensitive transistors;
left X, Y and Z axis scale reference scale means located in said left housing and respectively associated with said left scales and located between said respective scales and their respective first and second photosensitive transistors.

29. The device of claim 28 wherein:
said digitizing means includes voltage comparative means operatively associated with each of said respective photosensitive transistors.

* * * * *

United States Patent [19]

Hader

[11] Patent Number: 4,561,847
[45] Date of Patent: Dec. 31, 1985

[54] DENTAL ANCHORING FOR ATTACHMENT OF DENTAL PROSTHESES TO CROWNS, PIVOT TEETH, BRIDGES, AND SPLINT ELEMENTS

[76] Inventor: Helmut Hader, Les Allees 25, 2300 La Chaux-de-Fonds, Switzerland

[21] Appl. No.: 599,667

[22] Filed: Apr. 12, 1984

[30] Foreign Application Priority Data

May 9, 1983 [CH] Switzerland ............................ 2509/83

[51] Int. Cl.⁴ ............................................. A61C 13/22
[52] U.S. Cl. .................................................... 433/182
[58] Field of Search ................. 433/181, 182, 194, 193

[56] References Cited

U.S. PATENT DOCUMENTS 1,393,767 10/1921 Elslin ..................................... 433/191
4,196,516 4/1980 Poveromo ............................. 433/182

Primary Examiner—Robert Peshock
Attorney, Agent, or Firm—Young & Thompson

[57] ABSTRACT

The T-attachment in dovetail form comprises a patrix (1) mounted in the remainder of the teeth, as well as a matrix (2). The matrix (2) has no internal core but rather consists of a shell form making it possible, in the manufacture of the removable prosthesis by the casting method, to establish connection between the matrix (2) and the prosthesis by filling the shell form (3) with a casting material. The T-attachment is usable as dental anchoring for the attachment of dental prostheses to crowns, pivot teeth, bridges, and splint elements.

9 Claims, 8 Drawing Figures

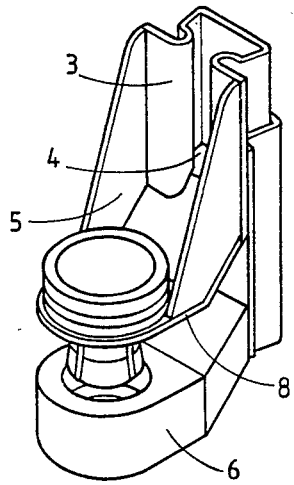

UNITED STATES PATENT AND TRADEMARK OFFICE
CERTIFICATE OF CORRECTION

PATENT NO. : 4,561,846

DATED : December 31, 1985

INVENTOR(S) : Joseph F. Polizzotto

It is certified that error appears in the above-identified patent and that said Letters Patent is hereby corrected as shown below:

```
Column 1, line 37, "train" should read --strain--.
Column 1, line 40, "device" should be --devices--.
Column 3, line 21, "said " second occurrence should be --side--.
Column 4, line 35, "signal"should be --signals--.
Column 4, line 43, "movemeent" should be --movement--.
Column 5, line 15, "transmittors" should be --transmitters--.
Column 6, line 13, "Approximate" should be --Appropriate--.
Column 6, line 15, "24 and 22" should be --22 and 24--.
Column 9, line 25, "transistors" should be --transistor--.
Column 9, line 40, "potion" should be --portion--.
Column 12, line 24, "298" should be --208--.
Column 12, line 50, "amd" should be --and--.
Column 13, line 47, "amd" should be --and--.
Column 14, line 11, "arrry" should be --array--.
Column 14, line 46, "maxilary" should be --maxillary--.
Column 15, line 37, "maxilary" should be --maxillary--.
```

Signed and Sealed this

Twentieth Day of May 1986

[SEAL]

Attest:

DONALD J. QUIGG

Attesting Officer

Commissioner of Patents and Trademarks